US010010655B2

(12) United States Patent
Zhao

(10) Patent No.: US 10,010,655 B2
(45) Date of Patent: Jul. 3, 2018

(54) DRUG DELIVERY DEVICE, METHOD, AND SYSTEM FOR ADMINISTRATION OF DUAL ANTIPLATELET THERAPY

(71) Applicant: Abbott Cardiovascular Systems Inc., Santa Clara, CA (US)

(72) Inventor: Weiying Zhao, Cupertino, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 32 days.

(21) Appl. No.: 13/840,402

(22) Filed: Mar. 15, 2013

(65) Prior Publication Data

US 2014/0277343 A1    Sep. 18, 2014

(51) Int. Cl.
*A61F 2/06* (2013.01)
*A61L 31/16* (2006.01)
*A61L 31/10* (2006.01)
*A61F 2/915* (2013.01)

(52) U.S. Cl.
CPC ........... *A61L 31/16* (2013.01); *A61L 31/10* (2013.01); *A61F 2/915* (2013.01); *A61F 2250/0067* (2013.01); *A61L 2300/42* (2013.01); *A61L 2300/45* (2013.01)

(58) Field of Classification Search
CPC ........ A61F 2/82; A61F 2/91; A61F 2002/072; A61F 2250/0067; A61L 31/16; A61L 33/0029; A61L 2300/602
USPC ............................................... 623/1.42, 1.46
See application file for complete search history.

(56) References Cited

U.S. PATENT DOCUMENTS

| | | | |
|---|---|---|---|
| 2003/0181973 A1* | 9/2003 | Sahota | 623/1.15 |
| 2010/0042206 A1* | 2/2010 | Yadav et al. | 623/1.42 |
| 2012/0010707 A1* | 1/2012 | Heyer et al. | 623/11.11 |
| 2012/0016467 A1* | 1/2012 | Chen et al. | 623/1.42 |

* cited by examiner

*Primary Examiner* — David Isabella
*Assistant Examiner* — Christine Nelson
(74) *Attorney, Agent, or Firm* — Womble Bond Dickinson (US) LLP

(57) ABSTRACT

A drug delivery device for reducing the likelihood of stent thrombosis following implantation in a subject is provided. A stent is provided including a body having a plurality of struts and one or more coatings applied to the body including at least one polymer, a therapeutic agent for inhibiting restenosis, a loading dose of a first antiplatelet agent and a maintenance dose of the first antiplatelet agent, and a loading dose of a second antiplatelet agent and a maintenance dose of the second antiplatelet agent.

20 Claims, 3 Drawing Sheets

DRUG DELIVERY DEVICE, METHOD, AND SYSTEM FOR ADMINISTRATION OF DUAL ANTIPLATELET THERAPY

FIELD OF THE DISCLOSED SUBJECT MATTER

The disclosed subject matter relates to a drug delivery device configured to treat blood vessels and a method for the device's use. Particularly, the present disclosed subject matter is directed to devices, methods, and systems for improving coronary luminal diameter of vessels in patients and for providing dual antiplatelet therapy during and after stent placement.

BACKGROUND

A leading cause of mortality within the developed world is cardiovascular disease. Coronary disease is of significant concern. Patients having such disease have narrowing in one or more coronary arteries. Generally, however, patients have narrowing in multiple coronary arteries. One treatment for the narrowing is stenting the blood vessel. Stenting involves the placement of a stent at the site of acute artery closure. This type of surgery has proved effective in restoring vessel patency and decreasing myocardial ischemia. However the exposure of currently used metallic stents to flowing blood can result in thrombus formation, smooth muscle cell proliferation and acute thrombotic occlusion of the stent.

Drug eluting stents ("DES") generally result in lower restenosis and revascularization rates as compared to bare metal stents in vessels having a diameter greater than approximately 3.0 mm ("large vessels"). However, vessels having a diameter of less than or less than 3.0 mm ("small vessels") continue to be clinically and angiographically at a disadvantage to larger vessels due to the inability of the small diameter to accommodate neointimal hyperplasia. These small-vessel DES have not led to significantly reduced late loss diameter or percent diameter stenosis like their large-vessel DES counterparts.

A safety concern associated with drug-eluting stents is the occurrence of stent thrombosis. For example, the polymer coatings and other aspects of DES may result in increased thrombogenicity. Dual antiplatelet therapy (DAPT), the administration of two anti-platelet medications, e.g., aspirin plus a $P2Y_{12}$ receptor inhibitor such a thienopyridine (clopidogrel or prasugrel) or a non-thienopyridine (ticagrelor), is one accepted strategy for minimizing the risk of stent thrombosis. To mitigate such risk, the American College of Cardiology Foundation (ACC)/American Heart Association (AHA) Task Force/Society for Cardiovascular Angiography and Interventions (SCAI) guideline recommends patients having percutaneous coronary intervention receive DAPT therapy prior to stent implantation, followed by twelve months of DAPT after the procedure. (See, e.g., Jneid H, Anderson J L, Wright R S, Adams C D, Bridges C R, Casey D E Jr, Ettinger S M, Fesmire F M, Ganiats T G, Lincoff A M, Peterson E D, Philippides G J, Theroux P, Wenger N K, Zidar J P. 2012 ACCF/AHA focused update of the guideline for the management of patients with unstable angina/non-ST-elevation myocardial infarction (UA/NSTEMI) (updating the 2007 guideline and replacing the 2011 focused update): a report of the American College of Cardiology Foundation/American Heart Association Task Force on Practice Guidelines. *J Am Coll Cardiol* 2012; 60:645-81.) (the "Guidelines") The Guidelines recommend a loading dose of $P2Y_{12}$ receptor inhibitor therapy for UA/NSTEMI patients for whom percutaneous coronary intervention ("PCI") is planned. The Guideline further recommend that one of the following regimens should be used: Clopidogrel 600 mg should be given as early as possible before or at the time of PCI; or prasugrel 60 mg should be given promptly and no later than 1 hour after PCI once coronary anatomy is defined and a decision is made to proceed with PCI; or ticagrelor 180 mg should be given as early as possible before or at the time of PCI.

The literature also suggested that the premature discontinuation of DAPT is also associated with stent thrombosis. Therefore, to mitigate the risk of stent thrombosis, the Guidelines further recommend patients who receive a DES be given aspirin indefinitely and a $P2Y_{12}$ receptor inhibitor for at least 12 months in the absence of increased risk of bleeding. The following duration and maintenance dose of $P2Y_{12}$ receptor inhibitor therapy is recommended: In UA/NSTEMI patients undergoing PCI, either clopidogrel 75 mg daily, prasugrel 10 mg daily, or ticagrelor 90 mg twice daily should be given for at least 12 months.

In real-world practice, however, many patients do not receive antiplatelet therapy at the time of stent implantation. In addition, non-compliance with the continuation of DAPT therapy after the procedure occurs, e.g., due to adverse events, invasive surgery, patient non-compliance with the prescribed therapy, etc. Most significantly, patients do not receive antiplatelet therapy at the site of the stent implantation. Rather, patients orally ingest a quantity of medication that is not targeted to the location of the potential thrombosis. Thus, there remains a need in the art for devices and methods for the addressing this concern, e.g., devices and system capable of delivering loading dose of DAPT at the site of stent deployment and providing a maintenance dose of DAPT at the site of stent deployment for a certain time following the procedure.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and devices particularly pointed out in the written description and claims thereof, as well as from the appended drawings.

In accordance with an aspect of the disclosed subject matter, an implantable stent is provided which includes a body including a plurality of struts; and one or more coatings applied to the body comprising at least one polymer; a therapeutic agent for inhibiting restenosis; a loading dose of aspirin and/or a $P2Y_{12}$ receptor inhibitor to tissue proximate the location of the implantable stent; and a maintenance dose of aspirin and/or a $P2Y_{12}$ receptor inhibitor provided to tissue proximate the location of the implantable stent.

In some embodiments, the first antiplatelet agent is selected from the group of aspirin and a $P2Y_{12}$ receptor inhibitor. In some embodiments, the second antiplatelet agent is selected from the group of aspirin and a $P2Y_{12}$ receptor inhibitor.

In some embodiments, the first antiplatelet agent is different from the second antiplatelet agent.

In some embodiments, the stent is configured for implantation inside a blood vessel and the maintenance dose of the first antiplatelet agent and the second antiplatelet agent are administered for at least approximately six months after implantation. In some embodiments, the stent is configured for implantation inside a blood vessel and the maintenance dose of the first antiplatelet agent and the second antiplatelet agent are administered for at least approximately twelve months after implantation.

A method for reducing a likelihood of stent thrombosis is provided which includes providing a stent having a body including a plurality of struts, and one or more coatings applied to the body including at least one polymer; a therapeutic agent for inhibiting restenosis; a loading dose of a first antiplatelet agent and a second antiplatelet agent and maintenance dose of the first antiplatelet agent and the second antiplatelet agent; implanting the stent inside a blood vessel of a subject; administering the loading dose of the first antiplatelet agent and the second antiplatelet agent to tissue proximate the implanted location of the stent; and administering the maintenance dose of the first antiplatelet agent and the second antiplatelet agent to tissue proximate the implanted location of the stent.

In some embodiments, the first antiplatelet agent is selected from the group of aspirin and a $P2Y_{12}$ receptor inhibitor. In some embodiments, the second antiplatelet agent is selected from the group of aspirin and a $P2Y_{12}$ receptor inhibitor.

In some embodiments, administering the maintenance dose includes administering the maintenance dose of the first antiplatelet agent and the second antiplatelet agent for six months. In some embodiments, administering the maintenance dose includes administering the maintenance dose of the first antiplatelet agent and the second antiplatelet agent for twelve months.

A dual antiplatelet therapy system is provided which includes an inflatable deployment device coated with a loading dose of a first antiplatelet agent and a loading dose of a second antiplatelet agent, the inflatable deployment device being configured to release the first and second loading dose when the inflatable deployment device is in an inflated configuration; and a stent disposed on the inflatable deployment device, the stent comprising a plurality of struts, a coating comprising at least one polymer adhered to the body, a therapeutic agent for inhibiting restenosis, and a maintenance dose of a third antiplatelet agent and a fourth antiplatelet agent, the stent being configured to continuously release the maintenance dose following an implantation of the stent within a subject.

In some embodiments, the first and third antiplatelet agents are selected from the group of aspirin and a $P2Y_{12}$ receptor inhibitor. In some embodiments, the second and fourth antiplatelet agents are selected from the group of aspirin and a $P2Y_{12}$ receptor inhibitor. In some embodiments, the second and fourth antiplatelet agents are different.

In some embodiments, the stent is configured for implantation inside a blood vessel and the maintenance dose of the third antiplatelet agent and the fourth antiplatelet agent are administered within the vessel for at least six months after implantation. In some embodiments, the stent is configured for implantation inside a blood vessel and the maintenance dose of the third antiplatelet agent and the fourth antiplatelet agent are administered within the vessel for at least twelve months after implantation.

A method for reducing a likelihood of stent thrombosis is provided including, providing an inflatable deployment device coated with a loading dose of a first antiplatelet agent and a loading dose of a second antiplatelet agent; providing a stent disposed on the inflatable deployment device, the stent comprising a plurality of struts, a coating comprising at least one polymer adhered to the body, a therapeutic agent for inhibiting restenosis, and a maintenance dose of a third antiplatelet agent and a fourth antiplatelet agent; administering the loading dose of the first and second antiplatelet agents upon inflation of the inflatable deployment device within a vessel of a patient; and administering the maintenance dose of the third and fourth antiplatelet agents after deployment of the stent within the vessel of the patient.

In some embodiments, the first and third antiplatelet agents are selected from the group of aspirin and a $P2Y_{12}$ receptor inhibitor. In some embodiments, the second and fourth antiplatelet agents are selected from the group of aspirin and a $P2Y_{12}$ receptor inhibitor. In some embodiments, the second and fourth antiplatelet agents are different.

In some embodiments, administering the maintenance dose includes administering the third and fourth antiplatelet agents for at least six months after implantation. In some embodiments, administering the maintenance dose includes administering the third and fourth antiplatelet agents for at least twelve months after implantation.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and device of the disclosed subject matter. Together with the description, the drawings serve to explain the principles of the disclosed subject matter.

DETAILED DESCRIPTION OF THE PREFERRED EMBODIMENT

Reference will now be made in detail to various embodiments of the disclosed subject matter, an example of which is illustrated in the accompanying drawings. The method and corresponding steps of the disclosed subject matter will be described in conjunction with the detailed description of the device.

The methods and devices presented herein are directed to a drug delivery device configured to treat a blood vessel and a method for the use of the device. In the described exemplary embodiments, methods and devices are directed to an intraluminal stent for improving coronary luminal diameter of small vessels in patients with symptomatic heart disease while mitigating risks associated with stent thrombosis.

Figure 1:
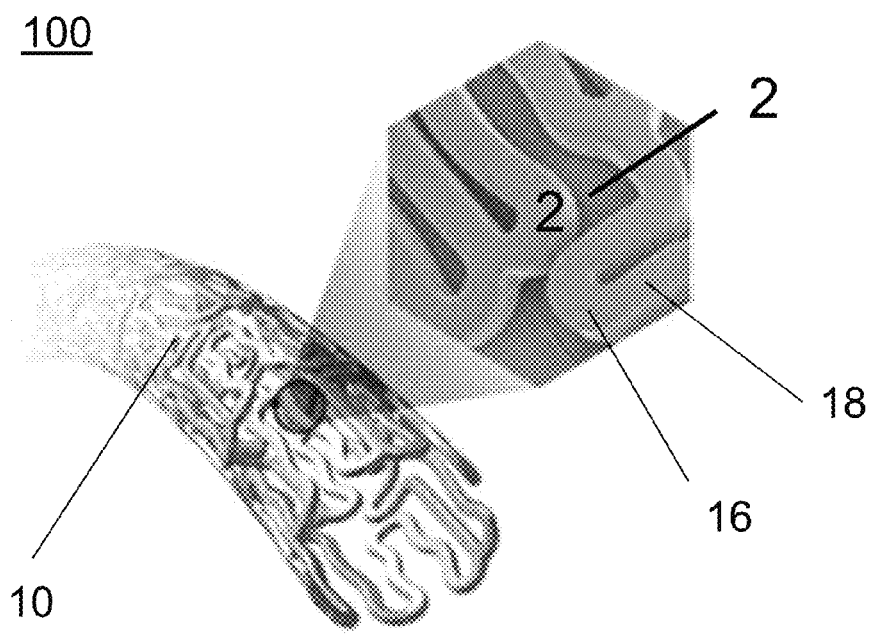
FIG. 1 is a schematic representation of the drug delivery device in accordance with the disclosed subject matter.
Figure 2:
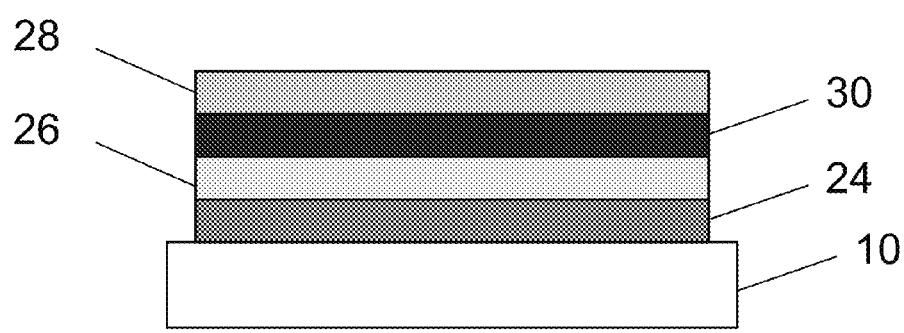
FIG. 2 is cross sectional view of a stent delivery device in accordance with the disclosed subject matter.
Figure 3:
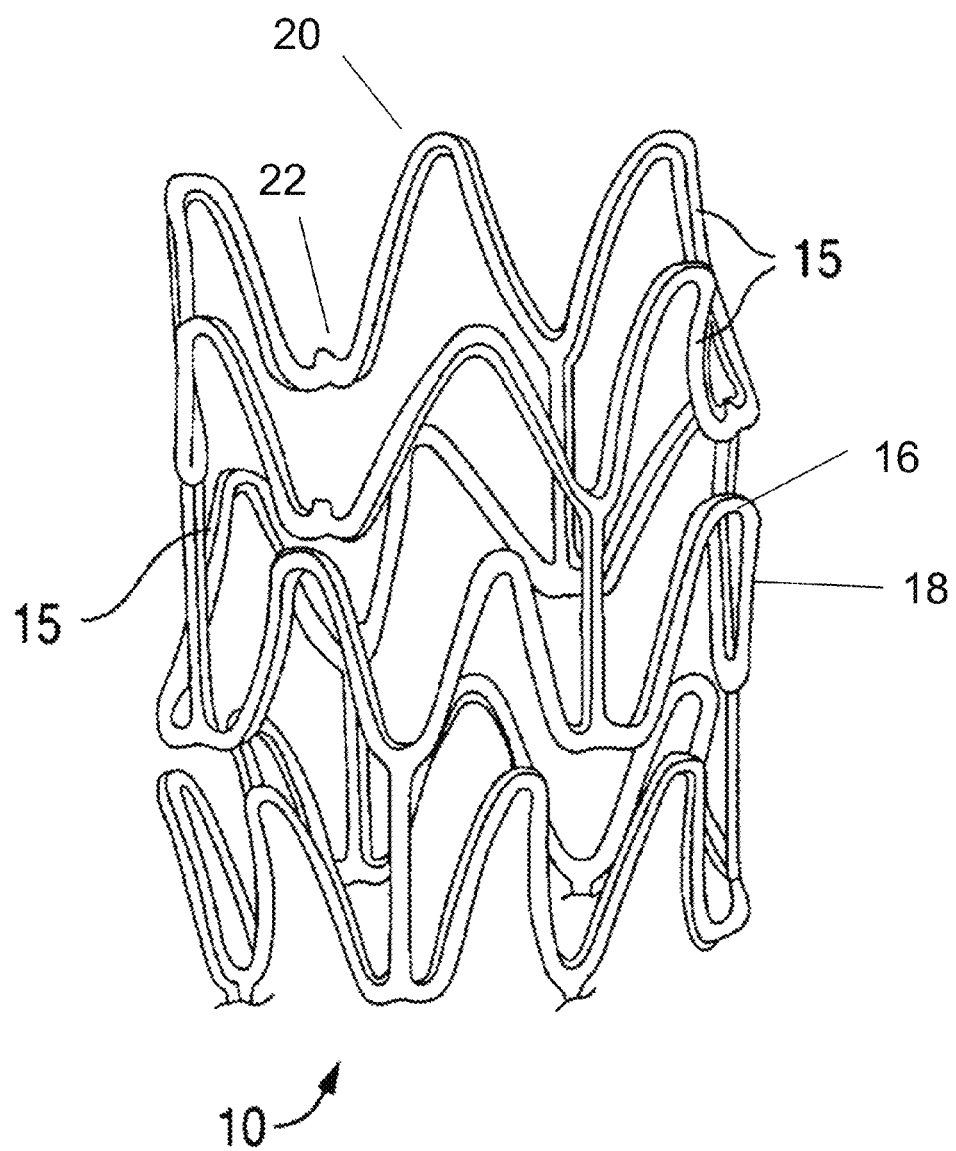
FIG. 3 is a schematic representation of an alternative geometry of a stent in accordance with the disclosed subject matter.

For purpose of explanation and illustration, and not limitation, a sample embodiment of a device in accordance with the disclosed subject matter is shown in FIGS. 1-3 and is designated generally by reference character 100. The device 100 generally includes an intraluminal base stent, including a stent body 10. As illustrated in the various embodiments shown in FIGS. 1-3, the stent can be configured in a variety of geometries. Although the device and methods associated with the present subject matter may be used in vessels of any size, for purposes of explanation and not limitation, the present disclosure discusses a stent suitable for use in small vessels, e.g., vessels having a diameter of less than or equal to approximately 3.0 mm and an axial length of approximately 12 mm. Prior to deployment the stent is crimped on a balloon, or other suitable expandable device. Crimping can be performed by pressurizing the balloon while the stent is radially compressed onto the balloon with a crimping apparatus. Once the stent has reached its radially compressed configuration, the pressure within the balloon can be released, while an inward crimping force exerted on the stent by the crimping apparatus is maintained. After a dwell time, the inward crimping force can be discontinued, and the balloon and crimped stent are removed from the crimping apparatus. As a result of the crimping process, balloon material extends radially outward through interstices of the stent to facilitate stent retention on the balloon while advancing the stent delivery catheter through a vessel lumen.

The expanded diameter of the stent ranges from about 2.25 mm at lower balloon inflation pressures (e.g., about 8 atm) to about 2.59 mm at higher balloon inflation pressures (e.g., about 16 atm). In various embodiments, the base stent is designed for use in small vessels having diameters of greater than or equal to approximately 2.25 mm to 2.5 mm. The stent body 10 is preferably but not necessarily balloon expandable and may be fabricated from any suitable metallic material including, e.g., stainless steel, tantalum, nickel-titanium, cobalt-chromium, titanium, shape memory and superelastic alloys, and the noble metals such as gold or platinum, as described in U.S. Pat. No. 6,939,373, which is herein incorporated by reference in its entirety. Alternatively, a self-expanding stent can be employed wherein the stent automatically expands at the desired location within the lumen by retracting a sheath on the delivery catheter. In some embodiments, the stent body is fabricated from L-605 cobalt chromium (CoCr) alloy. In other embodiments, the stent body 10 can be described more particularly as having a series of interconnected strut members which define a plurality of first peaks, second peaks, and valleys disposed therebetween. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery.

Such a small-vessel stent is used in patients who have narrowing in small coronary arteries that are greater than or equal to 2.25 mm to less than or equal to 2.50 mm in diameter and where the affected length of the artery is less than or equal to 28 mm long.

As shown in FIGS. 1 and 3, stent body 10 is made up of a plurality of cylindrical rings 15 which extend circumferentially around the stent when it is in a tubular form. The stent has a delivery catheter outer shaft diameter of 0.032" distally and 0.026" proximally. Each cylindrical ring has a cylindrical ring proximal end and a cylindrical ring distal end. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 15 defines a cylindrical plane which is a plane defined by the proximal and distal ends of the ring and the circumferential extent as the cylindrical ring travels around the cylinder. Each cylindrical ring includes cylindrical outer wall surface which defines the outermost surface of the stent, and cylindrical inner wall surface which defines the innermost surface of the stent. The cylindrical plane follows the cylindrical outer wall surface.

In keeping with the invention, an undulating link is positioned within cylindrical plane. The undulating links connect one cylindrical ring 15 to an adjacent cylindrical ring 15 and contribute to the overall longitudinal flexibility to the stent due to their unique construction. The flexibility of the undulating links derives in part from curved portion 16 connected to straight portions 18 In the exemplary embodiment shown in FIG. 1, the straight portions are substantially perpendicular to the longitudinal axis of the stent. Thus, as the stent is being delivered through a tortuous vessel, such as a coronary artery, the curved portions 16 and straight portions 18 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

The stent body 10 can be described more particularly as having a plurality of peaks 20 and valleys 22, as shown in FIG. 3. Although the stent is not divided into separate elements, for ease of discussion references to peaks and valleys is appropriate. Each of the cylindrical rings 15 has a plurality of peaks 20 which have struts 18 attached to an apex. The struts can be either curved or straight depending upon the particular application.

The stent body 10 can be made in many ways. One exemplary method of making the stent is to cut a thin-walled tubular member, and to remove portions of the tubing in the desired pattern for the stent, leaving. In some embodiments, the tubing is cut in the desired pattern by means of a machine-controlled laser as is well known in the art. In some embodiments, the struts have a thickness of less than approximately 110 μm. In a specific embodiment, the struts have a thickness of 81 μm.

As illustrated in FIG. 2, in some embodiments, the base stent body 10 is coated with active and inactive ingredients. The inactive ingredient(s) can include polymers 24, e.g., poly(N-acetylglucosamine) (Chitin), Chitosan, poly(-hydroxyvalerate), poly(D,L-lactide-co-glycolide), poly(1-lactide-co-glycolide) poly(-hydroxybutyrate), poly(-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), poly(vinylidene fluoride), poly(vinylidene fluoride-co-hexafluoropropylene), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids. In a specific embodiment, the inactive ingredients are the polymers poly n-butyl methacrylate (PBMA) and PVDF-HFP, which is comprised of vinylidene fluoride and hexafluoropropylene monomers. PVDF-HFP is a non-erodible semi-crystalline random copolymer with a molecular weight of 254,000 to 293,000 daltons. PBMA is a homopolymer with a molecular weight of 264,000 to 376,000 daltons.

The active ingredient(s) may include a therapeutic agent that can include any substance capable of exerting a therapeutic or prophylactic effect. Examples of therapeutic agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1, actinomycin X1, and actinomycin C1. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, thienopyridine, low molecular weight heparins, heparinoids, hirudin, argatroban, forskolin, vapiprost, prostaglandin (and analogues), prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, COX inhibitors, and thrombin and thromboxane inhibitors such as Angiomax a (Biogen, Inc., Cambridge, Mass.), phosphodiesterase inhibitors, vitamin K antagonists, etc.

Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

In some embodiments an active agent is a therapeutic agent for inhibiting restenosis 26, e.g., everolimus. Everolimus, developed by Novartis Pharma AG, is a proliferation signal inhibitor, or mTOR inhibitor. It is a semi-synthetic macrolide immunosuppressant, synthesized by chemical modification of rapamycin (sirolimus). Everolimus has been shown to inhibit in-stent neointimal growth in coronary vessels following stent implantation due to its anti-proliferative properties.

In some embodiments, PBMA, which adheres well with metallic materials and other polymers, is used as a primer to coat the base stent. PVDF-HFP is used as a drug matrix that is mixed with everolimus. The PVDF-HFP/everolimus mixture is adhered to the surface of the PBMA coated stent. In a specific embodiment, this PVDF-HFP/everolimus mixture comprises 83% polymer and 17% everolimus. The thickness of the polymer coating is less than approximately 10 μm. In a specific embodiment, the thickness of the polymer coating is 7.1 μm. The concentration of the everolimus in the copolymer is about 50 μg/cm$^2$ to about 150 μg/cm$^2$. In a specific embodiment the concentration of the everolimus in the copolymer is 100 μg/cm$^2$. Systems and methods for coating stents are disclosed in U.S. Pat. No. 8,003,157, which is herein incorporated by reference.

In some embodiments, DAPT is incorporated into the coating(s) applied to the body of the stent, e.g, in another coating to the active agent or in the same coating as the active agent. For example, two antiplatelet agents, e.g., aspirin with a P2Y$_{12}$ receptor inhibitor, could be coated on the surface of the stent. Exemplary thienopyridine P2Y$_{12}$ receptor inhibitor medications include, e.g., clopidogrel (trade name Plavix®, Bristol-Myers Squibb and Sanofi) or prasugrel (trade name Effient™, or Efient™, Daiichi Sankyo Co., Ube, Eli Lilly and Company). In another embodiment, aspirin and ticagrelor (trade name Brilinta™, Brilique™, or Possia™, AstraZeneca) can be used as the second antiplatelet agents. The two antiplatelet agents may be applied in equal or differing concentrations, as so desired in order to accommodate the particular patient's needs and health risks.

During stent deployment, a loading dose of both antiplatelet agents is delivered to the vessel as the stent expands to engage the lumen walls proximate (adjacent) the location where the stent is implanted. The loading dose for clopidogrel is 600 mg, for prasugrel is 60 mg, and for ticagrelor is 180 mg. By introducing the loading dose to the affected site directly (rather than orally), the antiplatelet effect of the DAPT occurs without significant delay, and further allows the loading dose to be reduce to lower amounts.

Further, DAPT is slowly released proximate the location where the stent is implanted over an extended period of time as a maintenance dose 30, e.g., during the period of time when the risk of stenosis is the highest. The maintenance dose for aspirin is 75-100 mg daily. For clopidogrel, the maintenance dose is 75 mg daily; for prasugrel the maintenance dose is 10 mg daily; and for ticagrelor the maintenance dose is 180 mg daily. The DAPT is released over the extended period of time using slow release techniques. Some devices are "matrix" type, and consist of the active compound dispersed in a matrix of carrier material. The carrier material may be either porous or non-porous, solid or semi-solid, and permeable or impermeable to the active compound. Matrix devices may be biodegradable, i.e., they may slowly erode after administration. Alternatively, matrix devices may be nondegradable, and rely on diffusion of the active compound through the walls or pores of the matrix. Other devices are "reservoir" type, and consist of a central reservoir of active compound surrounded by a rate controlling membrane. The membrane may be either porous or non-porous, but is not usually biodegradable. Some sustained release devices are hybrids, having a matrix core surrounded by a rate controlling membrane. Other sustained release devices may be mechanical in nature, and include small compound-filled electrical or osmotic pumps. Such configurations are designed to release the DAPT at a rate equivalent to the maintenance daily dose, e.g., as described above.

In some embodiments, the maintenance dose of DAPT is released over a period of thirty days when the risk of stent thrombosis is the highest. In other embodiments, the DAPT medication could be released to the vessel at the maintenance dose of DAPT for approximately an extended period of time, e.g., six months, nine months, one year.

Figure 4:
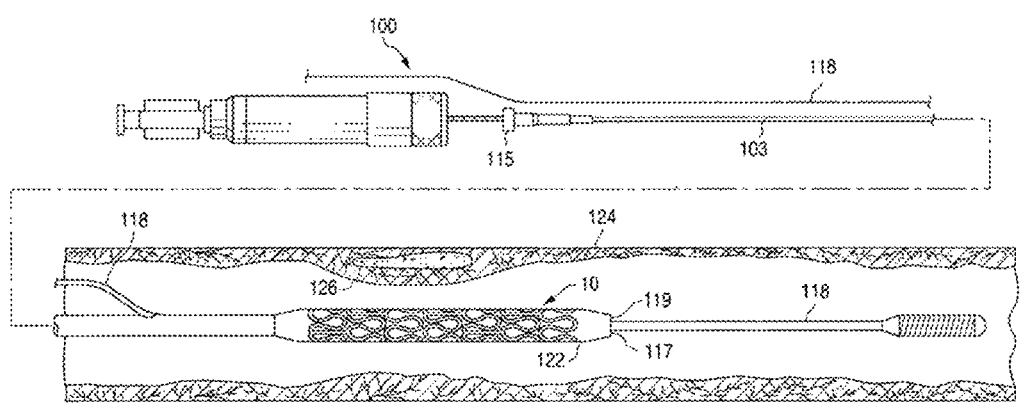
FIG. 4 is a schematic representation of a stent delivery system in accordance with the disclosed subject matter.

FIG. 4 depicts stent 10 mounted on a stent delivery assembly 100 which is used to deliver the stent and implant it in an artery 124, peripheral artery, or other vessel or lumen within the body. Stent delivery assembly 100 shown in FIG. 4 includes a catheter 103 which has a proximal end 115 and a distal end 117. The stent delivery assembly 100 is configured to advance through the patient's vascular system by advancing over a guide wire by any of the well known methods. Stent delivery assembly 100 as depicted in FIG. 4 includes a port where a guide wire 118 will exit the catheter. The distal end of the guide wire 118 exits catheter distal end 119 so that the catheter 103 advances along the guide wire 118 on a section of the catheter between the port and the catheter distal end 119. Stent 10 is mounted on an expandable member 122 (balloon) and is crimped tightly thereon so that stent 100 and expandable member 122 present a low profile diameter for delivery through the coronary arteries.

In a typical procedure to implant stent 10, guide wire 118 is advanced through the patient's vascular system by well-known methods so that the distal end of the guide wire is advanced past a diseased area 126. Thereafter, stent delivery assembly 100 is advanced over the guide wire so that the stent assembly is positioned in the target area. Expandable member or balloon 122 is inflated by well-known means so that it expands radially outwardly and in turn expands the stent 10 radially outwardly until the stent is apposed to the vessel wall. The expandable member is then deflated and the catheter withdrawn from the patient's vascular system.

Radiopaque balloon markers may be used to position the stent across the lesion. Angiography may be used to confirm stent position. If the position of the stent is not optimal, it should be carefully repositioned or removed. The balloon markers indicate both the stent edges and the balloon shoulders. Expansion of the stent should not be undertaken if the stent is not properly positioned in the target lesion. Then, the rotating hemostatic valve should be tightened.

Next, the stent may be deployed. In some embodiments, the stent is deployed slowly by pressurizing the delivery system in 2 atm increments, every 5 seconds, until completely expanded. Accepted practice generally targets an initial deployment pressure that would achieve a stent inner diameter ratio of about 1.1 times the reference vessel diameter. In some embodiments, pressure is maintained for 30 seconds. If necessary, the delivery system can be repressurized or further pressurized to assure complete apposition of the stent to the artery wall. The entire lesion and balloon treated area (including dissections) should be covered with the stent, allowing for adequate stent coverage into healthy tissue proximal and distal to the lesion. The balloon is then deflated by withdrawing the inflation medium (e.g., liquid, air or some other gas) from the inflation device for 30 seconds.

Post procedure, when crossing a newly deployed stent with an intravascular ultrasound (IVUS) catheter, a coronary guide wire, a balloon catheter or delivery system, care should be exercised to avoid disrupting the stent placement, apposition, geometry, and/or coating.

In some embodiments, DAPT may be incorporated into the design of the deployment balloon. For example, two antiplatelet agents (e.g., aspirin and a $P2Y_{12}$ receptor inhibitor) could be coated on the surface of the stent balloon. During stent deployment, the balloon is inflated to expand the vessel such that a loading dose of both antiplatelet agents is delivered to the vessel at the exact location where the stent is implanted. In some embodiments, the loading dose is released from the balloon within approximately ten minutes of inflation. The two antiplatelet agents may be applied in equal or differing concentrations, as so desired in order to accommodate the particular patient's needs and health risks.

In some embodiments, the loading dose of DAPT is coated on the balloon portion of the delivery catheter (e.g., in addition or alternative to the stent body and/or the stent balloon). Pre-dilation and post-dilation are common practice during stent implantation, wherein a balloon (or other expandable device) is expanded before and after the delivery of the stent, respectively. A loading dose of DAPT disposed on the exterior surface of the balloon could be delivered during pre-dilation or post-dilation with a DAPT-coated balloon catheter when the balloon is expanded (thereby increasing the surface area of the balloon, and in turn the amount of DAPT exposed) and engages the lumen walls. Alternatively, in a combined system including both a dilation balloon (intended for dilating the vessel prior to or post delivery of the stent) and a stent balloon (which expands to deliver the stent), the loading dose of DAPT could be coated on the dilation balloon instead of on the stent balloon, and a thin layer of top coating with DAPT maintenance dose could be applied on the stent itself. In some embodiments, the maintenance dose is continuously released from the stent after stent implantation.

The stent continuously releases the maintenance dose over at least five days following an implantation of the stent within vessel.

In some embodiments, a dual antiplatelet therapy system is provided which includes an inflatable deployment device, e.g., a balloon 122. The inflatable deployment device is coated with a loading dose of a first antiplatelet agent and a loading dose of a second antiplatelet agent. The inflatable deployment device can entirely release the loading doses of the first antiplatelet agent and the second antiplatelet agent when the inflatable deployment device is in an inflated configuration, e.g., in less than ten minutes when positioned in an inflated configuration. The first and second antiplatelet agents include aspirin and a $P2Y_{12}$ receptor inhibitor. A stent 10 disposed on the inflatable deployment device includes a plurality of struts, described above, and one or more coatings. The coatings can include at least one polymer adhered to the body of the stent, a therapeutic agent for inhibiting restenosis, and a maintenance dose of a third antiplatelet agent and a fourth antiplatelet agent. The third and fourth antiplatelet agents include aspirin and a $P2Y_{12}$ receptor inhibitor. The first and third antiplatelet agents can be the same or different. The second and fourth antiplatelet agents could be the same or different. In some embodiments, the loading dose of the second antiplatelet agent is clopidogrel and the maintenance dose of the fourth antiplatelet agent is ticagrelor. The stent continuously releases the maintenance dose following an implantation of the stent within a subject. In some embodiments, the maintenance dose is released over six months. In some embodiments, the maintenance dose is released over twelve months.

With any of the above DAPT coatings on individual components or combination of components, this system described herein will be able to provide both a loading dose at the time of initial implantation and a maintenance dose of DAPT afterwards. Such a configuration helps ensure compliance with the use of DAPT loading dose and maintenance dose. Additionally, because the drug is delivered at the exact location of stent, the dose required may be lower compared with a systemic administration because a more concentrated dose may be provided within the local area of stent. Local dosing may further help reduce systemic effects such as risk of bleeding. Also, because the DAPT is provided without patient intervention or action, such administration obviates the need for the patient to remember to take the medications daily.

A study demonstrated that discontinuation of DAPT therapy at a time greater than six months from stent implantation produces stent thrombosis at rates similar to those observed when DAPT therapy is never discontinued. These rates are significantly less than when DAPT therapy is discontinued less than six months from stent implantation. For example, the XIENCE V® everolimus-eluting stent is a drug eluting stent. The safety and efficacy of XIENCE V® has been demonstrated in previous randomized trials. Clinical data from the two large trials of XIENCE V® (SPIRIT IV and XIENCE V® USA), both suggest that this new drug eluting stent might be safe with short-term DAPT therapy.

The SPIRIT IV trial is a prospective, randomized, single-blinded, multicenter US clinical trial evaluating XIENCE V® EECSS against the TAXUS® EXPRESS® paclitaxel-eluting stent. A total of 3687 patients were enrolled with 2458 patients randomized to XIENCE V® stent arm. The two year stent thrombosis (ARC definite/probable) rate was 0.42% in the XIENCE V® arm. In patients receiving XIENCE V stents, the stent thrombosis rate was about 0.3% in patients who discontinued thienopyridine after six months and was also about 0.3% for those who did not discontinue the therapy. On the other hand, for patients who discontinued thienopyridine before six months, the stent thrombosis rate was significantly higher at 2.4%.

The XIENCE V® USA was a large, prospective, multi-center, single-arm study that examined the safety of XIENCE V® in an unselected, real-world population. A total of 5054 patients were enrolled. The overall 1-year stent thrombosis (ARC definite/probable) rate is 0.84%. In the standard risk cohort and the extended risk cohort, there was no stent thrombosis after DAPT interruption beyond 6 months in the overall population. In the standard-risk cohort (a population similar to SPIRIT IV), there was no late stent thrombosis after DAPT interruption at any time after implantation. More specifically, in those patients where there was no DAPT interruption, the late stent thrombosis rate was 0.15% (2/1305) for the standard risk cohort, 0.50% (11/2195) for the extended risk cohort, and 0.37% (13/3500) for the overall cohort. In those patients where there was DAPT interruption within 6 months, the late stent thrombosis rate was 0.0% (0/118) for the standard risk cohort, 1.2% (3/251) for the extended risk cohort, and 0.81% (3/369) for the overall cohort. In those patients where there was DAPT interruption after 6 months, the late stent thrombosis rate was 0.0% (0/122) for the standard risk cohort, 0.0% (0/170) for the extended risk cohort, and 0.0% (0/292) for the overall cohort. These clinical results support the safety of short term DAPT (6 months) use with the XIENCE V® stent, especially in less complex patients with a low risk of stent thrombosis.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and device of the disclosed subject matter without departing from the spirit or scope of the disclosed subject matter. Thus, it is intended that the disclosed subject matter include modifications and variations that are within the scope of the appended claims and their equivalents.

The invention claimed is:
1. An implantable stent comprising:
a body including a plurality of struts;
a primer coating on the struts;
a polymer layer over the primer coating;
a therapeutic agent layer over the polymer layer, wherein the therapeutic agent layer includes a therapeutic agent to inhibit restenosis;
a first dual antiplatelet therapy (DAPT) coating layer over the therapeutic agent layer, the first DAPT coating layer including a combined loading dose of a first antiplatelet agent and a second antiplatelet agent, wherein the first DAPT coating layer releases the combined loading dose when the body is delivered into a blood vessel, and wherein the first antiplatelet agent is clopidogrel; and a second DAPT coating layer between the therapeutic agent layer and the first DAPT coating layer, the second DAPT coating layer including a combined daily maintenance dose of the first antiplatelet agent and the second antiplatelet agent, wherein the second DAPT coating layer releases the combined daily maintenance dose after the first DAPT coating layer releases the combined loading dose;

wherein an amount of the first antiplatelet agent in the first DAPT coating layer is different than an amount of the first antiplatelet agent in the second DAPT coating layer.

2. The stent of claim 1, wherein the implantable stent is configured for implantation inside the blood vessel, and wherein the combined daily maintenance dose of the first antiplatelet agent and the second antiplatelet agent are administered for at least approximately six months after implantation.

3. The stent according to claim 1, wherein the implantable stent is configured for implantation inside the blood vessel, and wherein the combined daily maintenance dose of the first antiplatelet agent and the second antiplatelet agent are administered for at least approximately twelve months after implantation.

4. The apparatus of claim 1, wherein the amount of the first antiplatelet agent in the first DAPT coating layer is up to 600 mg.

5. The apparatus of claim 1, wherein the second antiplatelet agent is an aspirin and the amount of the second antiplatelet agent in the second DAPT coating layer is up to 100 mg per day.

6. The apparatus of claim 1, wherein the amount of the first antiplatelet agent in the second DAPT coating layer is up to 75 mg per day.

7. The implantable stent of claim 1, wherein the amount of the first antiplatelet agent in the first DAPT coating layer is less than the amount of the first antiplatelet agent in the second DAPT coating layer, wherein a loading dose of the first antiplatelet agent in the first DAPT coating layer has a higher delivery rate than a maintenance dose of the first antiplatelet agent in the second DAPT coating layer, wherein the loading dose is delivered during stent deployment, and wherein the maintenance dose is delivered over a period of at least thirty days after stent deployment.

8. The implantable stent of claim 1, wherein a loading dose of the first antiplatelet agent in the first DAPT coating layer is up to 8 times a maintenance dose of the first antiplatelet agent in the second DAPT coating layer, wherein the loading dose is delivered during stent deployment, and wherein the maintenance dose is delivered over a period of at least thirty days after stent deployment.

9. An implantable stent comprising:
a body including a plurality of struts;
a primer coating on the struts;
a polymer layer over the primer coating;
a therapeutic agent layer over the polymer layer, wherein the therapeutic agent layer includes a therapeutic agent to inhibit restenosis;
a first dual antiplatelet therapy (DAPT) coating layer over the therapeutic agent layer, the first DAPT coating layer including a combined loading dose of a first antiplatelet agent and a second antiplatelet agent, wherein the first DAPT coating layer releases the combined loading dose when the body is delivered into a blood vessel, wherein the first antiplatelet agent is prasugrel; and a second DAPT coating layer between the therapeutic agent layer and the first DAPT coating layer, the second DAPT coating layer including a combined daily maintenance dose of the first antiplatelet agent and the second antiplatelet agent, wherein the second DAPT coating layer releases the combined daily maintenance dose after the first DAPT coating layer releases the combined loading dose;

wherein an amount of the first antiplatelet agent in the first DAPT coating layer is different than an amount of the first antiplatelet agent in the second DAPT coating layer.

10. The stent of claim 9, wherein the implantable stent is configured for implantation inside the blood vessel, and wherein the combined daily maintenance dose of the first antiplatelet agent and the second antiplatelet agent are administered for at least approximately six months after implantation.

11. The stent according to claim 9, wherein the implantable stent is configured for implantation inside the blood vessel, and wherein the combined daily maintenance dose of the first antiplatelet agent and the second antiplatelet agent are administered for at least approximately twelve months after implantation.

12. The apparatus of claim 9, wherein the amount of the first antiplatelet agent in the first DAPT coating layer is up to 60 mg.

13. The apparatus of claim 9, wherein the second antiplatelet agent is an aspirin and the amount of the first antiplatelet agent and the second antiplatelet agent in the second DAPT coating layer is up to 100 mg per day.

14. The apparatus of claim 9, wherein the amount of the first antiplatelet agent in the second DAPT coating layer is up to 10 mg per day.

15. An implantable stent comprising:
a body including a plurality of struts;
a primer coating on the struts;
a polymer layer over the primer coating;
a therapeutic agent layer over the polymer layer, wherein the therapeutic agent layer includes a therapeutic agent to inhibit restenosis;
a first dual antiplatelet therapy (DAPT) coating layer over the therapeutic agent layer, the first DAPT coating layer including a combined loading dose of a first antiplatelet agent and a second antiplatelet agent, wherein the first DAPT coating layer releases the combined loading dose when the body is delivered into a blood vessel, wherein the first antiplatelet agent is ticagrelor; and a second DAPT coating layer between the therapeutic agent layer and the first DAPT coating layer, the second DAPT coating layer including a combined daily maintenance dose of the first antiplatelet agent and the second antiplatelet agent, wherein the second DAPT coating layer releases the combined daily maintenance dose after the first DAPT coating layer releases the combined loading dose;

wherein an amount of the first antiplatelet agent in the first DAPT coating layer is different than an amount of the first antiplatelet agent in the second DAPT coating layer.

16. The stent of claim 15, wherein the implantable stent is configured for implantation inside the blood vessel, and wherein the combined daily maintenance dose of the first antiplatelet agent and the second antiplatelet agent are administered for at least approximately six months after implantation.

17. The stent according to claim 15, wherein the implantable stent is configured for implantation inside the blood vessel, and wherein the combined daily maintenance dose of the first antiplatelet agent and the second antiplatelet agent are administered for at least approximately twelve months after implantation.

18. The apparatus of claim 15, wherein the amount of the second antiplatelet agent in the first DAPT coating layer is up to 180 mg.

19. The apparatus of claim 15, wherein the second antiplatelet agent is an aspirin and the amount of the first antiplatelet agent and the second antiplatelet agent in the second DAPT coating layer is up to 100 mg per day.

20. The apparatus of claim 15, wherein the amount of the first antiplatelet agent in the second DAPT coating layer is up to 180 mg per day.

* * * * *